(12) United States Patent
Yang et al.

(10) Patent No.: US 11,980,546 B1
(45) Date of Patent: May 14, 2024

(54) VALVE ANNULUS CONTRACTION SURGICAL SYSTEM WITH ADJUSTABLE ANNULUS CONTRACTING FORCE AT SINGLE POINT

(71) Applicant: CREATIVE MEDTECH (BEIJING) CO., LTD, Beijing (CN)

(72) Inventors: Fan Yang, Beijing (CN); Wei Zheng, Beijing (CN); Wuen Han, Beijing (CN)

(73) Assignee: CREATIVE MEDTECH (BEIJING) CO., LTD, Beijing (CN)

( * ) Notice: Subject to any disclaimer, the term of this patent is extended or adjusted under 35 U.S.C. 154(b) by 0 days.

(21) Appl. No.: 18/431,991

(22) Filed: Feb. 4, 2024

(30) Foreign Application Priority Data

May 11, 2023 (CN) .......................... 202310523949.9

(51) Int. Cl.
*A61F 2/24* (2006.01)
(52) U.S. Cl.
CPC .......... *A61F 2/2466* (2013.01); *A61F 2/2445* (2013.01); *A61F 2220/0016* (2013.01)
(58) Field of Classification Search
CPC ........ A61F 2/2442–2448; A61F 2/2466; A61F 2220/0016
See application file for complete search history.

(56) References Cited

U.S. PATENT DOCUMENTS

| | | |
|---|---|---|
| 9,877,833 B1 | 1/2018 | Bishop et al. |
| 2014/0155993 A1 | 6/2014 | Kapadia |
| 2018/0055630 A1 | 3/2018 | Patel et al. |
| 2018/0318082 A1 | 11/2018 | Manash |
| 2024/0065837 A1* | 2/2024 | Hoffer .................. A61F 2/2454 |

FOREIGN PATENT DOCUMENTS

| | | |
|---|---|---|
| CN | 102686185 A | 9/2012 |
| CN | 106573129 A | 4/2017 |
| CN | 110664515 A | 1/2020 |
| CN | 110913801 A | 3/2020 |
| CN | 111467082 A | 7/2020 |
| CN | 111481250 A | 8/2020 |

(Continued)

OTHER PUBLICATIONS

Notice of Allowance of counterpart Chinese Patent Application No. 202310523949.9 issued on Jul. 19, 2023.

(Continued)

*Primary Examiner* — William H Matthews (57) ABSTRACT

The present application provides a valve annulus contraction surgical system with an adjustable annulus contracting force at a single point, and relates to the technical field of medical devices. The system includes a plurality of anchors, an implantation device, a plurality of groups of locking sutures and a suture locking device. A suture locking tab is arranged on at least one of two sides of each of the anchors. The implantation device is configured to implant the anchors into a valve annulus; each group of locking sutures includes a first locking suture and a second locking suture for connection with the suture locking tab. The suture locking device is configured to lock and fix the other end of the first locking suture and the other end of the second locking suture. In the present application, a valve orifice can be completely covered by a valve, thereby ensuring a therapeutic effect.

6 Claims, 11 Drawing Sheets

(56) References Cited

FOREIGN PATENT DOCUMENTS

| | | |
|---|---|---|
| CN | 111481251 A | 8/2020 |
| CN | 111568605 A | 8/2020 |
| CN | 112741711 A | 5/2021 |
| CN | 113116428 A | 7/2021 |
| CN | 114681137 A | 7/2022 |
| CN | 115024863 A | 9/2022 |
| CN | 115399921 A | 11/2022 |

OTHER PUBLICATIONS

First Office Action of counterpart Chinese Patent Application No. 202310523949.9 issued on Jun. 30, 2023.

* cited by examiner

FIG. 14

VALVE ANNULUS CONTRACTION SURGICAL SYSTEM WITH ADJUSTABLE ANNULUS CONTRACTING FORCE AT SINGLE POINT

CROSS REFERENCE TO RELATED APPLICATIONS

The present application claims the benefit of Chinese Patent Application No. 202310523949.9 filed on May 11, 2023, the contents of which are incorporated herein by reference in their entirety.

TECHNICAL FIELD

The present application relates to the technical field of medical devices, and in particular, to a valve annulus contraction surgical system with an adjustable annulus contracting force at a single point.

BACKGROUND ART

A valve, a mitral valve, a tricuspid valve, etc. in a disease state cannot be closed completely, which leads to various heart diseases. Valve surgery is to force the valve to be closed completely by means of an implantation device, so that blood circulation of each ventricle and atrium of the heart is smooth, thus treating heart diseases.

Generally, the implantation device mostly fixes a formed annulus body to a valve annulus. The formed annulus body is elastic, and can be contracted by pulling a thread in the formed annulus body, so that the valve annulus is contracted with a formed annulus. After the valve annulus is contracted, the valve can completely cover a valve orifice, thus achieving complete closure of the valve.

However, as the formed annulus body described above is in a preset shape, if the valve annulus is deformed significantly and greatly, it is difficult to contract the valve annulus completely with the shape of the formed annulus. As a result, it is still difficult to cover the valve orifice completely by the valve after the surgery.

SUMMARY OF THE INVENTION

An embodiment of the present application provides a valve annulus contraction surgical system with an adjustable annulus contracting force at a single point, to solve at least the problem of it being still difficult to cover a valve orifice completely by a valve after an existing implantation device completes implanting.

In a first aspect, an embodiment of the present application provides a valve annulus contraction surgical system with an adjustable annulus contracting force at a single point, the valve annulus contraction surgical system comprising: a plurality of anchors, wherein a suture locking tab is arranged on at least one of two sides of each of the anchors; an implantation device configured to implant the anchors into a valve annulus; a plurality of groups of locking sutures, wherein each group of locking sutures comprises a first locking suture and a second locking suture, one end of the first locking suture is connected to the suture locking tab of one of two adjacent anchors, and one end of the second locking suture is connected to the suture locking tab of the other of the two adjacent anchors; and a suture locking device configured to lock and fix the other end of the first locking suture and the other end of the second locking suture.

In some embodiments of the present application, each of the anchors comprises a mating portion and an implantable portion that are connected to each other, wherein the mating portion is configured to be connected to and mated with the implantation device, and the implantable portion is a spiral thread; and the suture locking tab is provided with a plurality of first connecting holes for the spiral thread in a length direction of the suture locking tab, and is provided with a second connecting hole for the first locking suture or the second locking suture to pass through.

In some embodiments of the present application, the implantation device comprises an implantation tube, an implantation operation assembly, a delivery cable, a puncture needle, and a puncture operation assembly; the delivery cable is partially located in the implantation tube, and is driven by the implantation operation assembly such that the anchor is moved to and released at an opening of the implantation tube; the puncture needle penetrates the delivery cable, and has one end provided with a tip, and the other end connected to the puncture operation assembly; and the puncture operation mechanism is configured to drive the tip to extend out of the opening of the implantation tube.

In some embodiments of the present application, the puncture operation assembly comprises a puncture handle and a limiting mechanism; the puncture handle is connected to an end of the puncture needle that faces away from the tip; and the limiting mechanism is located between the implantation operation assembly and the puncture handle, and is connected to an end of the delivery cable that is located outside the implantation tube, wherein the limiting mechanism is configured to limit a length of the puncture needle extending out of the opening of the implantation tube.

In some embodiments of the present application, the suture locking device comprises a suture locking apparatus and a suture locking operation handle; and the suture locking apparatus is configured to lock and cut off the first locking suture and the second locking suture of the group of locking sutures under the driving of the suture locking operation handle.

In some embodiments of the present application, the suture locking apparatus comprises a housing, a pressing assembly, and a cutting assembly; the pressing assembly, the cutting assembly and the suture locking operation handle are connected to one another in sequence; and the suture locking operation handle is configured to drive the pressing assembly to lock the first locking suture and the second locking suture, and drive the cutting assembly to cut the first locking suture and the second locking suture.

In some embodiments of the present application, the housing is provided at one end with a first threaded hole, a first opening for entry of the first locking suture, and a second opening for the second locking suture to pass through, and at the other end with a third opening for the first locking suture and the second locking suture to extend out; the pressing assembly comprises a first stud and a locking suture pressing block; the first stud is connected to the first threaded hole, and is provided with a second threaded hole; the locking suture pressing block is sleeved on the first stud; the first stud is driven by the suture locking operation handle to rotate, such that the locking suture pressing block and an inner wall surface of the housing lock the first locking suture and the second locking suture; the cutting assembly comprises a second stud and a locking suture cutting block; the locking suture cutting block is rotatably sleeved on the second stud, and the second stud is connected to the second threaded hole; and the suture locking operation handle drives the locking suture cutting block to rotate to cut the first locking suture and the second locking suture, and the suture locking operation handle drives the second stud to rotate such that the second stud and the locking suture cutting block are separated from the housing.

In some embodiments of the present application, the suture locking operation handle comprises an outer tube, a first rotating shaft, and a second rotating shaft; the first rotating shaft is mounted in the outer tube, and has one end connected to the second stud; the second rotating shaft is hollow, is sleeved on the first rotating shaft, and has one end connected to the locking suture cutting block, wherein the first rotating shaft drives the first stud to rotate in a first circumferential direction, such that the locking suture pressing block and the inner wall surface of the housing press the first locking suture and the second locking suture; the first rotating shaft rotates in a second circumferential direction opposite to the first circumferential direction, such that the locking suture cutting block is located at a cutting position; and the second rotating shaft is configured to drive the locking suture cutting block at the cutting position to rotate for cutting.

In some embodiments of the present application, a suture locking plate opposite the locking suture pressing block is mounted at the inner wall surface of the housing; and the suture locking operation handle is configured to drive the locking suture pressing block to approach the suture locking plate, so as to press the first locking suture and the second locking suture.

In some embodiments of the present application, a cross-sectional shape of a side of the locking suture cutting block that faces the third opening has a first annular tip; a side wall of the housing at the third opening is provided with a second annular tip facing the locking suture cutting block; and the suture locking operation handle is configured to drive the first annular tip to approach the second annular tip to a cutting position for performing rotary cutting.

The valve annulus contraction surgical system with an adjustable annulus contracting force at a single point according to the embodiments of the present application differs from an annulus contracting method using a traditional formed annulus in that anchors are implanted at several predetermined positions on the valve annulus, a locking suture is arranged on one side or either side of each of the anchors, the locking sutures are used to lock the anchors in pairs, and since the level of locking of every two anchors may be different, the level of locking of two anchors may be arbitrarily adjusted according to the shape of the valve annulus in such a way that a valve orifice can be completely covered by a valve after the adjustment, thereby ensuring a therapeutic effect.

BRIEF DESCRIPTION OF THE DRAWINGS

Features, advantages and technical effects of exemplary embodiments of the present application will be described below with reference to accompanying drawings.

LIST OF REFERENCE SIGNS

100. Anchor; 110. Suture locking tab; 111. First connecting hole; 112. Second connecting hole; 120. Mating portion; 130. Implantable portion; 200. Implantation device; 210. Implantation tube; 220. Implantation operation assembly; 230. Delivery cable; 240. Puncture needle; 250. Puncture operation assembly; 251. Puncture handle; 252. Limiting mechanism; 2521. First portion; 25211. Slideway; 2522. Second portion; 25221. Sliding member; 300. Group of locking sutures; 310. First locking suture; 320. Second locking suture; 400. Suture locking device; 410. Suture locking apparatus; 411. Housing; 4111. First threaded hole; 4112. First opening; 4113. Second opening; 4114. Third opening; 4115. Second annular tip; 412. Pressing assembly; 4121. First stud; 4122. Locking suture pressing block; 4123. Pressing anti-return elastic fastener; 4124. Suture locking plate; 413. Cutting assembly; 4131. Second stud; 4132. Locking suture cutting block; 41321. First annular tip; 420. Suture locking operation handle; 421. Outer tube; 422. First rotating shaft; 423. Second rotating shaft; 424. First knob; 425. Second knob.

DETAILED DESCRIPTION OF EMBODIMENTS

The implementations of the present application will be further described in detail below with reference to the accompanying drawings and embodiments. The following detailed description of the embodiments and the accompanying drawings are used to illustrate the principle of the present application in an exemplary manner, but shall not be used to limit the scope of the present application. That is, the present application is not limited to the described embodiments.

An existing method of valve surgery is to implant a C-shaped formed annulus body on a valve annulus. The formed annulus body is elastic, and can be contracted by pulling a thread in a formed annulus, so that the valve annulus is contracted synchronously with the formed annulus body. After the valve annulus is contracted, the valve can completely cover a valve orifice, thus achieving complete closure of the valve. However, since the formed annulus is in a preset shape in this solution, if the valve annulus is deformed significantly and greatly, it is difficult to contract the valve annulus completely with the shape of the formed annulus. As a result, it is still difficult to cover the valve orifice completely by the valve after the surgery.

Another method is to implant a circle of anchors 100 on the valve annulus, with a single tightening suture passing through the circle of anchors 100. When tightened, the tightening suture acts on the circle of anchors 100 at the same time, so that the valve orifice undergoes annulus contraction under the action of the tightening suture and the circle of anchors 100. In fact, this solution is a variation of the solution using the formed annulus, and has the disadvantage that forces acting on the anchors 100 by the tightening suture are substantially the same, so that it is difficult to achieve annulus contraction of a seriously deformed valve annulus.

Therefore, in order to solve the disadvantages existing in the aforementioned implantation structures, this embodiment provides a valve annulus contraction surgical system with an adjustable annulus contracting force at a single point. The system comprises: a plurality of anchors 100, an implantation device 200, a plurality of groups of locking sutures 300, and a suture locking device 400.

A suture locking tab 110 is arranged on at least one of two opposite sides of each of the anchors 100 in this embodiment. The implantation device 200 in this embodiment is configured to implant the anchors 100 into a valve annulus. Each group of locking sutures 300 in this embodiment comprises a first locking suture 310 and a second locking suture 320. One end of the first locking suture 310 in this embodiment is connected to the suture locking tab 110 of one of two adjacent anchors 100, and one end of the second locking suture 320 in this embodiment is connected to the suture locking tab 110 of the other of the two adjacent anchors 100. The suture locking device 400 in this embodiment is configured to lock and fix the other end of the first locking suture 310 and the other end of the second locking suture 320.

In order to better understand the present application, embodiments of the present application will be described below with reference to FIGS. 1 to 14.

Figure 1:
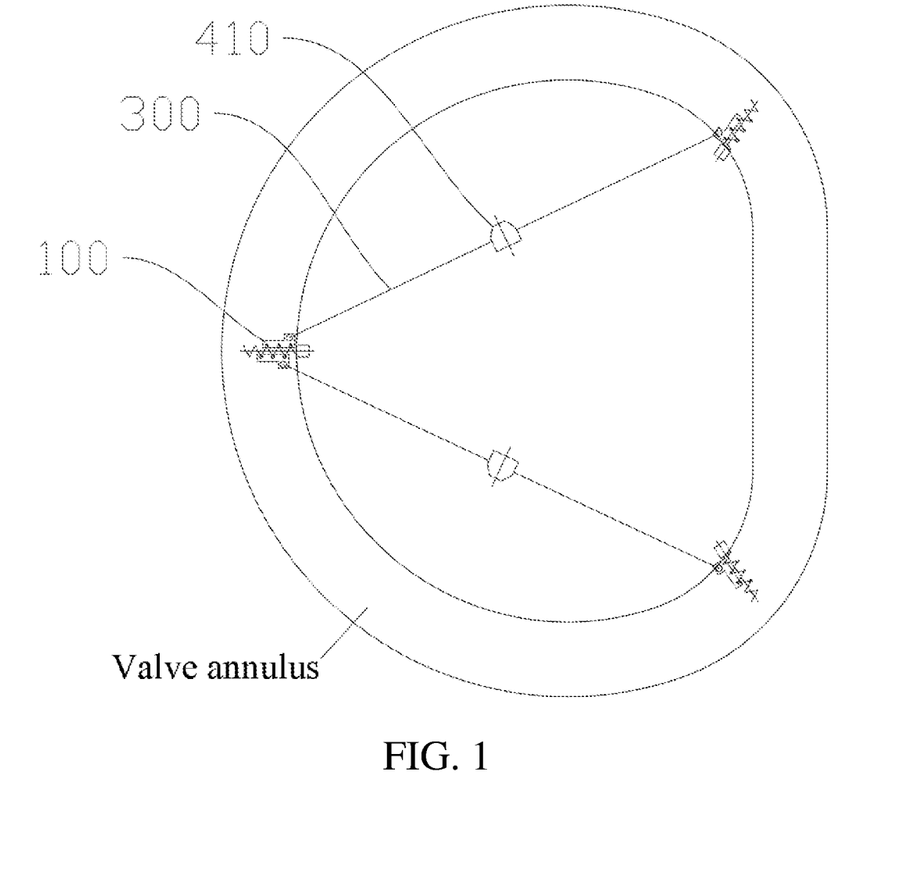
FIG. 1 is a schematic diagram of a first implementation of a valve annulus contraction surgical system with an adjustable annulus contracting force at a single point according to an embodiment of the present application after implantation of anchors and suture locking.

FIG. 1 is a schematic diagram of a first implementation of a valve annulus contraction surgical system with an adjustable annulus contracting force at a single point according to an embodiment of the present application after implantation of anchors 100 and suture locking. As shown in FIG. 1, the valve annulus contraction surgical system of this embodiment can implant three anchors 100 shown in the figure. One anchor 100 of the three anchors 100 is connected to each of the other two anchors 100 by means of a group of locking sutures 300. The groups of locking sutures 300 are used to lock the anchors 100 in pairs, and since the level of locking of every two anchors 100 may be different, the level of locking of two anchors 100 may be arbitrarily adjusted according to the shape of the valve annulus in such a way that a valve orifice can be completely covered by a valve after the adjustment, thereby ensuring a therapeutic effect.

Figure 2:
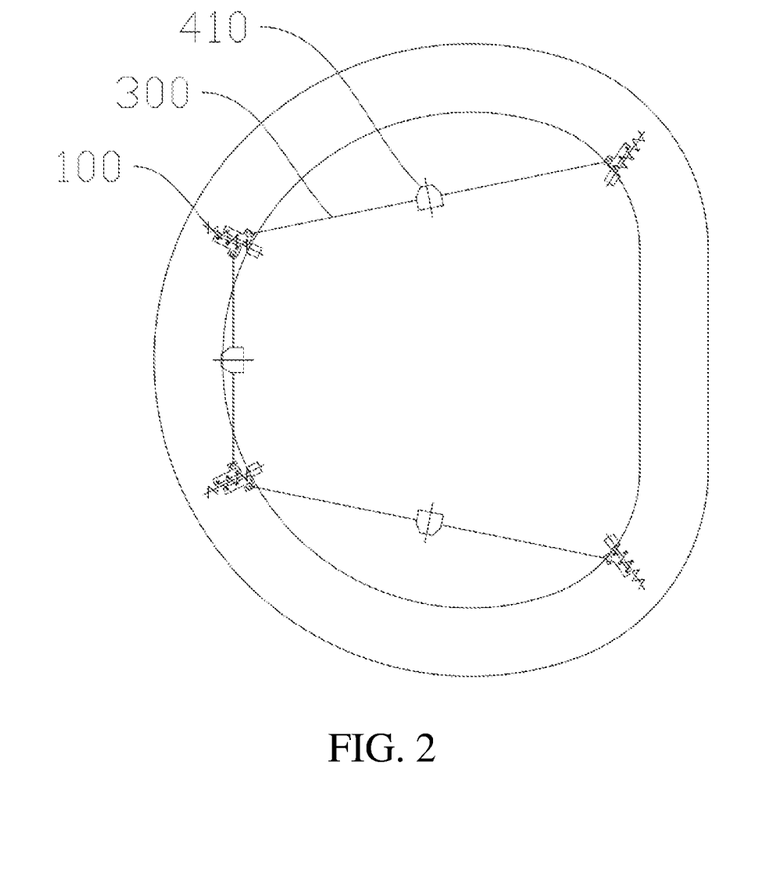
FIG. 2 is a schematic diagram of a second implementation of a valve annulus contraction surgical system with an adjustable annulus contracting force at a single point according to an embodiment of the present application after implantation of anchors and suture locking.

FIG. 2 is a schematic diagram of a second implementation of a valve annulus contraction surgical system with an adjustable annulus contracting force at a single point according to an embodiment of the present application after implantation of anchors 100 and suture locking. As shown in FIG. 2, the number of anchors 100 and the number of groups of locking sutures 300 may be determined as required. For example, every two of four anchors 100 shown in the figure are connected to each other by means of one group of locking sutures 300.

Figure 3:
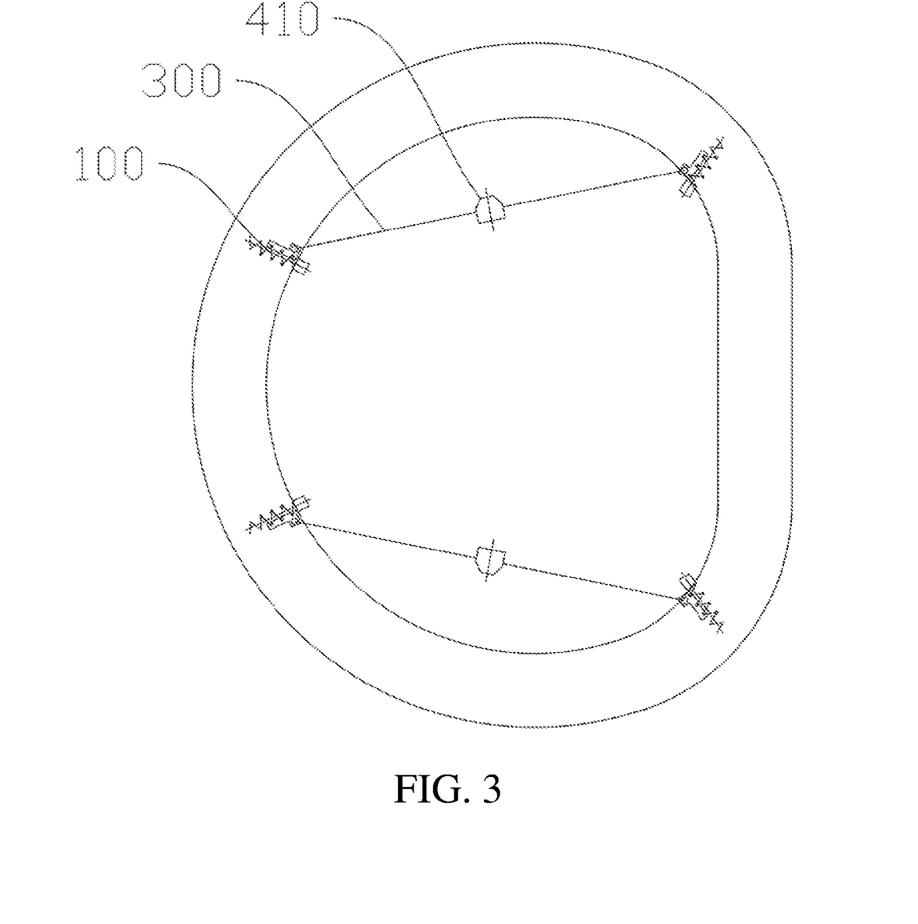
FIG. 3 is a schematic diagram of a third implementation of a valve annulus contraction surgical system with an adjustable annulus contracting force at a single point according to an embodiment of the present application after implantation of anchors and suture locking.

FIG. 3 is a schematic diagram of a third implementation of a valve annulus contraction surgical system with an adjustable annulus contracting force at a single point according to an embodiment of the present application after implantation of anchors 100 and suture locking. As shown in FIG. 3, the number of anchors 100 may be further increased, but it is possible to not connect every two adjacent anchors 100 to each other by means of a group of locking sutures 300.

Figure 4:
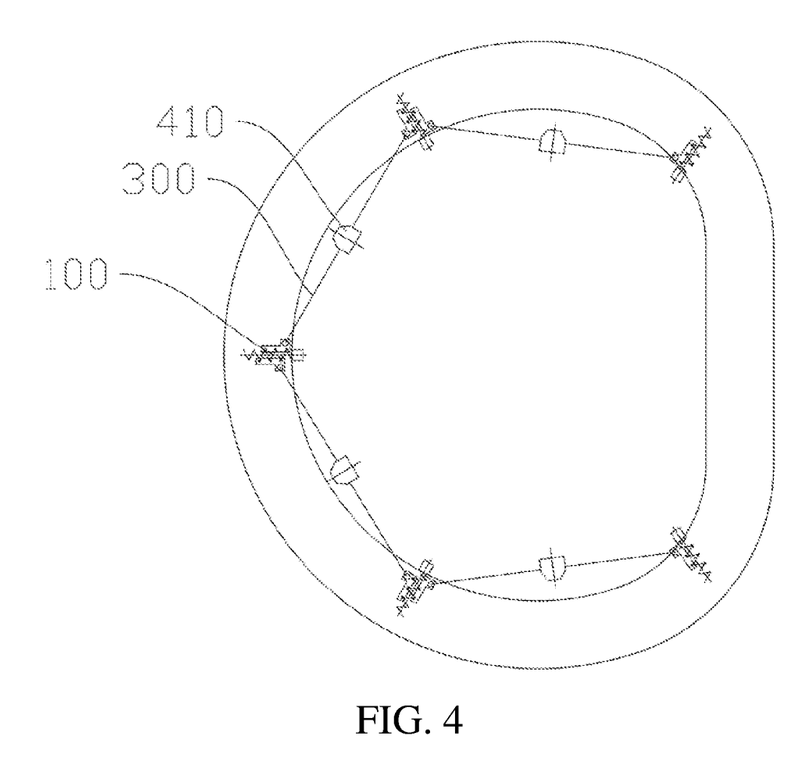
FIG. 4 is a schematic diagram of a fourth implementation of a valve annulus contraction surgical system with an adjustable annulus contracting force at a single point according to an embodiment of the present application after implantation of anchors and suture locking.
Figure 5:
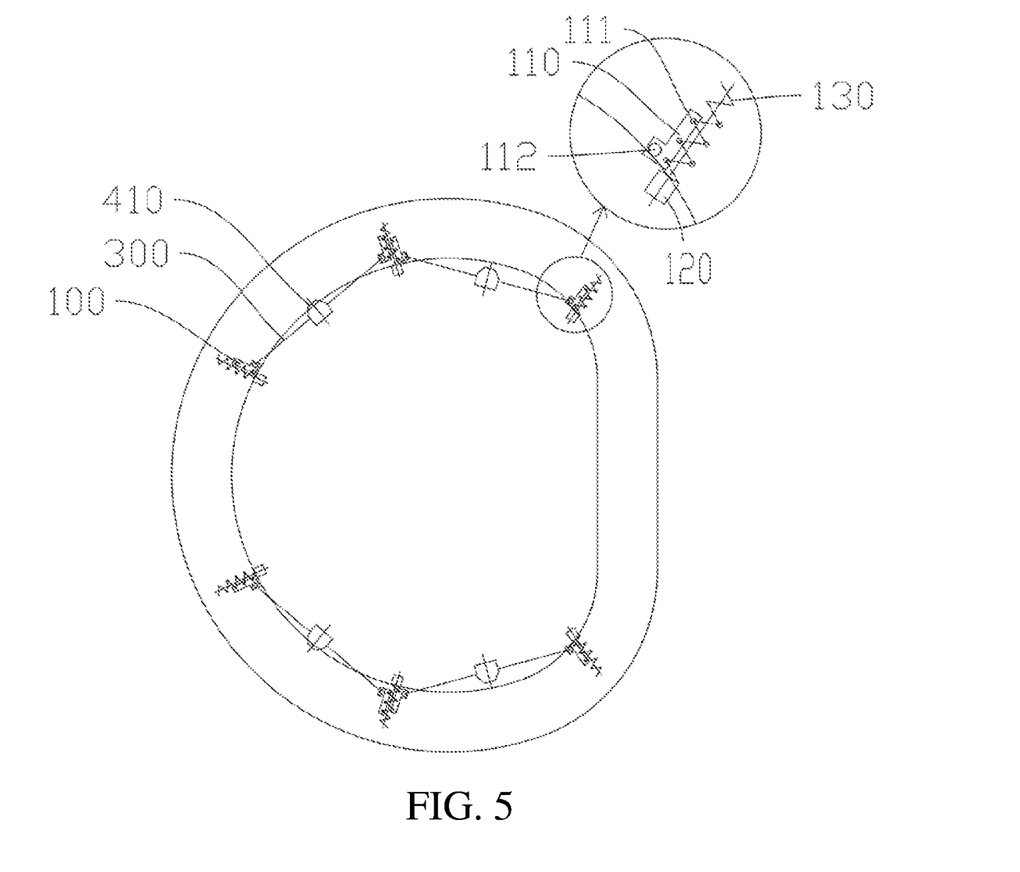
FIG. 5 is a schematic diagram of a fifth implementation of a valve annulus contraction surgical system with an adjustable annulus contracting force at a single point according to an embodiment of the present application after implantation of anchors and suture locking.

FIG. 4 is a schematic diagram of a fourth implementation of a valve annulus contraction surgical system with an adjustable annulus contracting force at a single point according to an embodiment of the present application after implantation of anchors 100 and suture locking, and FIG. 5 is a schematic diagram of a fifth implementation of a valve annulus contraction surgical system with an adjustable annulus contracting force at a single point according to an embodiment of the present application after implantation of anchors 100 and suture locking. As shown in FIGS. 4 and 5, the number of rivets may be further increased to five or six, and there may be four locking sutures as shown in the figure, that is, not every two adjacent anchors 100 must be connected to each other by means of a suture pressing assembly.

As shown in an enlarged view in FIG. 5, an anchor 100 and a group of locking sutures 300 described above may be connected to each other in such a way that the anchor 100 in this embodiment is designed to comprise a mating portion 120 and an implantable portion 130 that are connected to each other. The mating portion 120 is configured to be connected to and mated with the implantation device 200, and the implantable portion 130 is a spiral thread. Correspondingly, the suture locking tab 110 in this embodiment is provided with a plurality of first connecting holes 111 for the spiral thread in a length direction of the suture locking tab, and is provided with a second connecting hole 112 for the first locking suture 310 or the second locking suture 320 to pass through.

Figure 6:
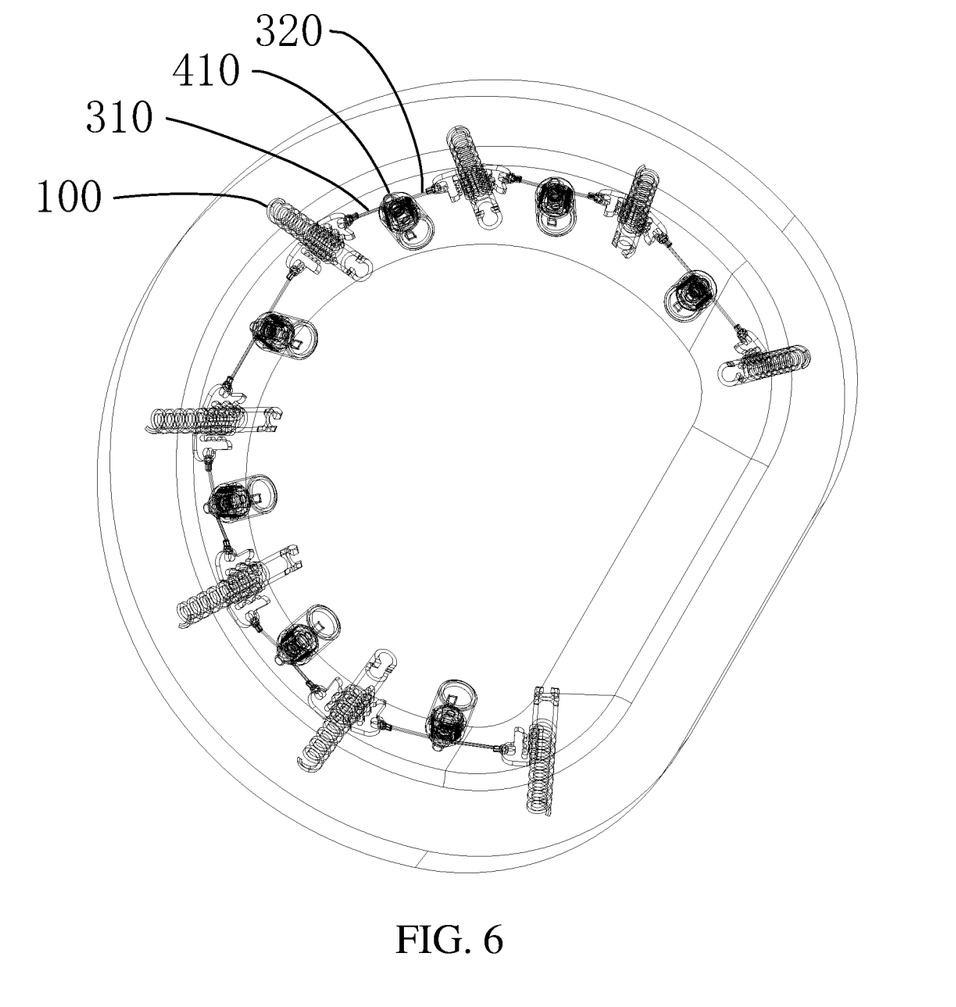
FIG. 6 is a schematic diagram of a sixth implementation of a valve annulus contraction surgical system with an adjustable annulus contracting force at a single point according to an embodiment of the present application after implantation of anchors and suture locking.

FIG. 6 is a schematic diagram of a sixth implementation of a valve annulus contraction surgical system with an adjustable annulus contracting force at a single point according to an embodiment of the present application after implantation of anchors 100 and suture locking. As shown in FIG. 6, after the surgery is performed by means of the valve annulus contraction surgical system of this embodiment, the structure of the system that is retained on the valve comprises the anchors 100, groups of locking sutures 300, and a suture locking apparatus 410 of a suture locking device 400.

Figure 7:
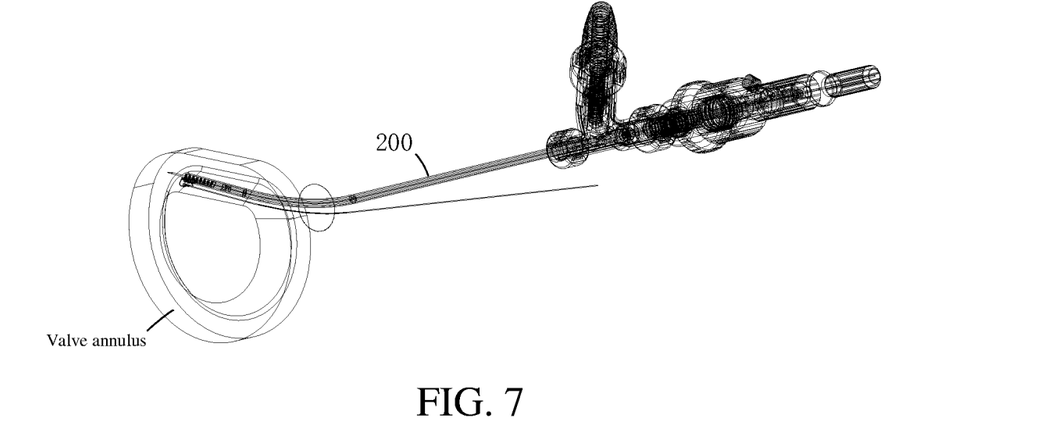
FIG. 7 is a schematic diagram of a valve annulus contraction surgical system with an adjustable annulus contracting force at a single point according to an embodiment of the present application with an anchor being implanted.

FIG. 7 is a schematic diagram of a valve annulus contraction surgical system with an adjustable annulus contracting force at a single point according to an embodiment of the present application with an anchor 100 being implanted. As shown in FIG. 7, when surgery is performed by means of the system of this embodiment, the anchor 100 is first implanted by means of an implantation device 200. The implantation device 200 may be any existing implantation device 200, and the existing structure is not described in this embodiment.

However, the applicant has found that when the anchor 100 is implanted by the existing implantation device 200, since a surface of the valve annulus is in an irregular saddle shape, and an actual surgical operation is guided by ultrasound, poor visual field display is caused, which leads to the problem of the delivered anchor 100 being not firmly fastened or the anchor 100 falling off, thereby impairing a therapeutic effect. Therefore, in this embodiment, a structural improvement is further performed on the implantation device 200.

Figure 8:
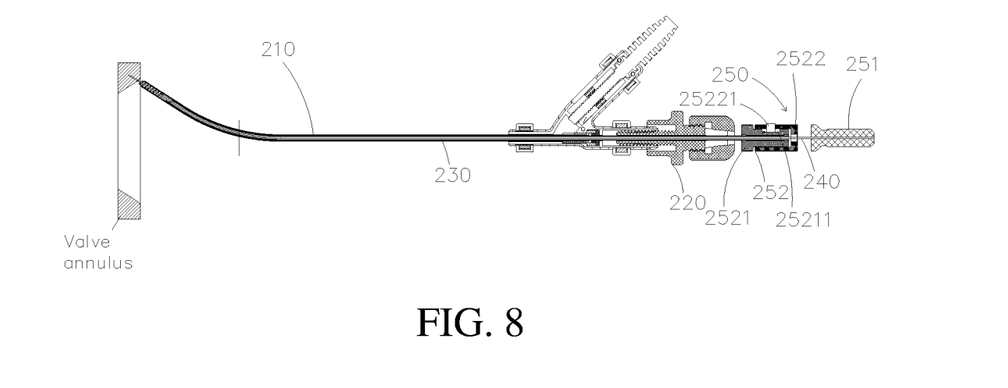
FIG. 8 is a schematic structural diagram of an implantation device of a valve annulus contraction surgical system with an adjustable annulus contracting force at a single point according to an embodiment of the present application.

FIG. 8 is a schematic structural diagram of an implantation device 200 of a valve annulus contraction surgical system with an adjustable annulus contracting force at a single point according to an embodiment of the present application. As shown in FIG. 8, the implantation device 200 in this embodiment comprises an implantation tube 210, an implantation operation assembly 220, a delivery cable 230, a puncture needle 240, and a puncture operation assembly 250. The implantation tube 210, the implantation operation assembly 220, the delivery cable 230, etc. in this embodiment are all of existing structures, and reference may be made to existing documents such as CN 111481251 A, CN 111568605 A, and CN 111481250 A. In this regard, no structural description or principle description is provided in this embodiment.

The delivery cable 230 in this embodiment is partially located in the implantation tube 210, and is driven by the implantation operation assembly 220 such that an anchor 100 is moved to and released at an opening of the implantation tube 210. The puncture needle 240 in this embodiment penetrates the delivery cable 230, and has one end provided with a tip, and the other end connected to the puncture operation assembly 250. The puncture operation mechanism in this embodiment is configured to drive the tip to extend out of the opening of the implantation tube 210.

As an implementation of this embodiment, the puncture operation assembly 250 in this embodiment comprises a puncture handle 251 and a limiting mechanism 252. The puncture handle 251 in this embodiment is connected to an end of the puncture needle 240 that faces away from the tip. The limiting mechanism 252 in this embodiment is located between the implantation operation assembly 220 and the puncture handle 251, and is connected to an end of the delivery cable 230 that is located outside the implantation tube 210. The limiting mechanism 252 is configured to limit a length of the puncture needle 240 extending out of the opening of the implantation tube 210.

Further, the limiting structure comprises a first portion 2521 and a second portion 2522 that are connected to each other. The second portion 2522 is located between the first portion 2521 and the puncture handle 251. Moreover, the second portion 2522 in this embodiment is configured to be movable from a first position to a second position on the first portion 2521 under the driving of the puncture handle 251. Moving from the first position to the second position, the puncture handle 251 drives the puncture needle 240 to extend out of the opening of the implantation tube 210 to a preset length.

Specifically, in this embodiment, an outer wall of the first portion 2521 is provided with a slideway 25211, and correspondingly, the second portion 2522 in this embodiment is sleeved on the first portion 2521 and is provided with a sliding member 25221 slidably connected to the slideway 25211. When the puncture handle 251 abuts against the second portion 2522 and drives the sliding member 25221 to move from one end to the other end of the slideway 25211, the puncture needle 240 extends out of the opening of the implantation tube 210 to the preset length.

Optionally, the slideway 25211 in this embodiment is a U-shaped groove, which has a first side portion and a second side portion (not shown) that are oppositely arranged in a length direction of the first portion 2521. When the second portion 2522 in this embodiment moves from the first position to the second position, the sliding member 25221 slides from the first side portion to the second side portion and is limited at the second side portion to fix the position of the second portion 2522 and determine a penetration depth of the puncture needle 240.

Figure 9:
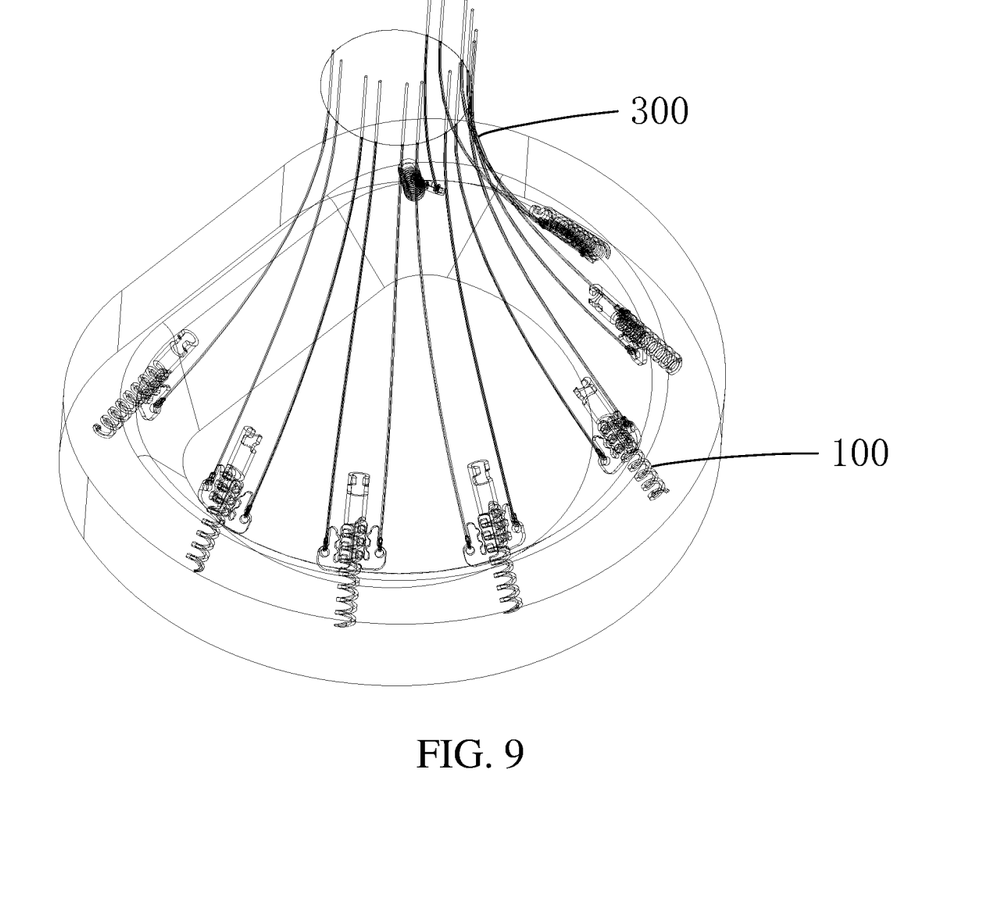
FIG. 9 is a schematic diagram showing a state of a valve annulus contraction surgical system with an adjustable annulus contracting force at a single point according to an embodiment of the present application after anchor delivery and before suture locking.

FIG. 9 is a schematic diagram showing a state of a valve annulus contraction surgical system with an adjustable annulus contracting force at a single point according to an embodiment of the present application after anchor delivery and before suture locking. As shown in FIG. 9, after the anchor 100 is implanted by means of the aforementioned implantation device 200, the first locking suture 310 and the second locking suture 320 on the anchor 100 are not connected to each other, and the first locking suture 310 and the second locking suture 320 need to penetrate into the suture locking device 400 in this embodiment by means of a suture penetrating structure (not shown) for suture locking and cutting.

Figure 10:
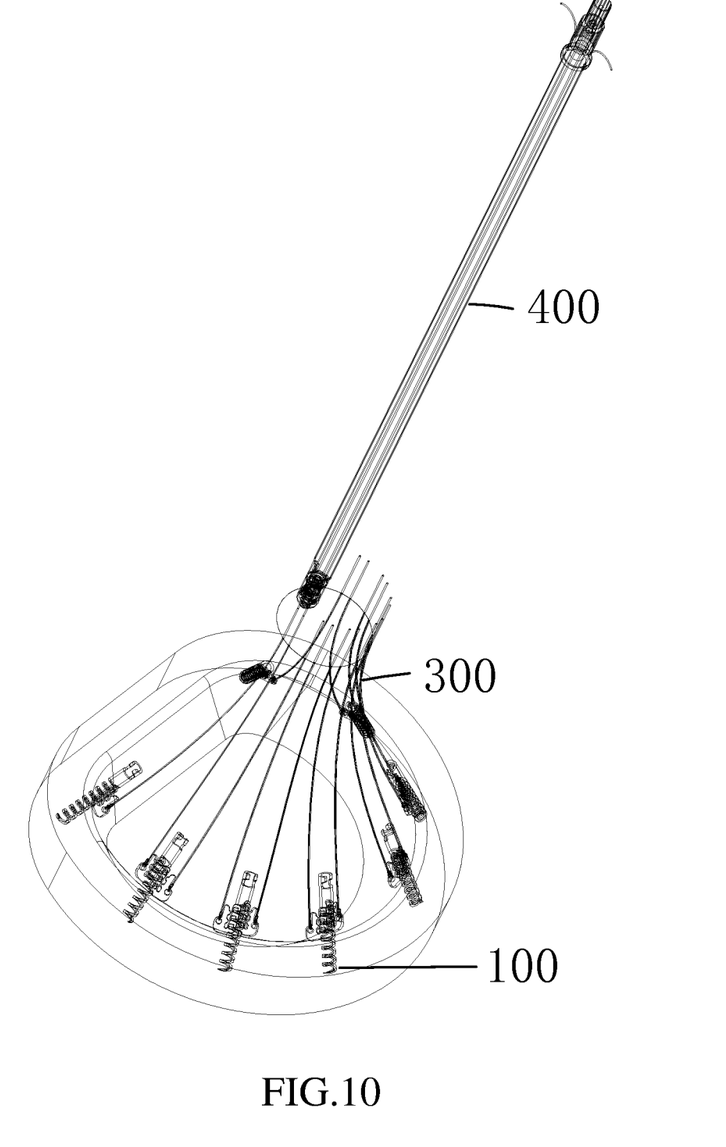
FIG. 10 is a schematic diagram showing a state of a valve annulus contraction surgical system with an adjustable annulus contracting force at a single point according to an embodiment of the present application during suture locking.

FIG. 10 is a schematic diagram showing a state of a valve annulus contraction surgical system with an adjustable annulus contracting force at a single point according to an embodiment of the present application during suture locking. As shown in FIG. 10, during the suture locking, the first locking suture 310 and the second locking suture 320 penetrate into the suture locking device 400 by using the suture penetrating structure. The suture locking device 400 includes a suture locking apparatus 410 and a suture locking operation handle 420 that are connected to each other, and the suture locking operation handle 420 can be disconnected from the suture locking apparatus 410.

The suture locking apparatus 410 in this embodiment is configured to lock and cut off the first locking suture 310 and the second locking suture 320 of the group of locking sutures 300 under the driving of the suture locking operation handle 420. After the cutting off, a partial structure of the suture locking apparatus 410 is retained in the valve annulus.

Figure 11:
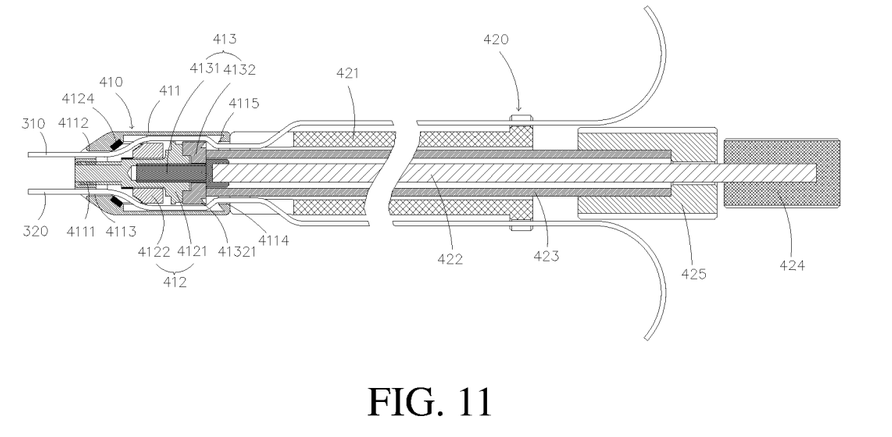
FIG. 11 is a schematic structural diagram of a suture locking device of a valve annulus contraction surgical system with an adjustable annulus contracting force at a single point according to an embodiment of the present application.

FIG. 11 is a schematic structural diagram of a suture locking device 400 of a valve annulus contraction surgical system with an adjustable annulus contracting force at a single point according to an embodiment of the present application. As shown in FIG. 11, in order to facilitate locking and cutting of the first locking suture 310 and the second locking suture 320, in this embodiment, the suture locking apparatus 410 is designed to comprise a housing 411, a pressing assembly 412, and a cutting assembly 413.

The housing 411 in this embodiment may allow an end of the first locking suture 310 and an end of the second locking suture 320 to penetrate and extend out. The pressing assembly 412 and the cutting assembly 413 in this embodiment are both mounted in the housing 411. The pressing assembly 412, the cutting assembly 413 and the suture locking operation handle 420 in this embodiment are connected to one another in sequence. Moreover, the suture locking operation handle 420 in this embodiment is configured to drive the pressing assembly 412 to lock the first locking suture 310 and the second locking suture 320, and drive the cutting assembly 413 to cut the first locking suture 310 and the second locking suture 320.

Further, in order to facilitate the penetration and extension-out of the first locking suture 310 and the second locking suture 320, and to facilitate the mounting of the pressing assembly 412 and the cutting assembly 413, the housing 411 in this embodiment is provided at one end with a first threaded hole 4111, a first opening 4112 for entry of the first locking suture 310, and a second opening 4113 for the second locking suture 320 to pass through, and at the other end with a third opening 4114 for the first locking suture 310 and the second locking suture 320 to extend out.

Correspondingly, the pressing assembly 412 in this embodiment comprises a first stud 4121 and a locking suture pressing block 4122. Specifically, the first stud 4121 in this embodiment comprises a threaded portion and a mounting portion with a radial dimension greater than that of the threaded portion. The threaded portion of the first stud 4121 is connected to the first threaded hole 4111, and the mounting portion is provided with a second threaded hole.

The locking suture pressing block 4122 in this embodiment is sleeved on the first stud 4121, and is fixedly connected to and rotates synchronously with the first stud 4121. The first stud 4121 in this embodiment is driven by the suture locking operation handle 420 to rotate, such that the locking suture pressing block 4122 and an inner wall surface of the housing 411 lock the first locking suture 310 and the second locking suture 320.

The cutting assembly 413 in this embodiment comprises a second stud 4131 and a locking suture cutting block 4132. The locking suture cutting block 4132 in this embodiment is rotatably sleeved on the second stud 4131, and the second stud 4131 is connected to the second threaded hole. The suture locking operation handle 420 in this embodiment drives the locking suture cutting block 4132 to rotate to cut the first locking suture 310 and the second locking suture 320, and the suture locking operation handle 420 drives the second stud 4131 to rotate such that the second stud 4131 and the locking suture cutting block 4132 are separated from the housing 411.

As shown in FIG. 11, in some embodiments, the suture locking operation handle 420 in this embodiment comprises an outer tube 421, a first rotating shaft 422, a second rotating shaft 423, a first knob 424, a second knob 425 and other functional components.

Among the aforementioned functional components, the outer tube 421 may be made of a steel wire and a polymer material. The first rotating shaft 422 in this embodiment is mounted in the outer tube 421, one end of the first rotating shaft 422 is connected to the second stud 4131, and the other end of the first rotating shaft 422 is fixedly connected to the first knob 424. The second rotating shaft 423 in this embodiment is hollow and is sleeved on the first rotating shaft 422. The second rotating shaft 423 has one end connected to the locking suture cutting block 4132, and the other end fixedly connected to the second knob 425.

When it is necessary to perform suture locking, the first knob 424 is rotated, and thus the first rotating shaft 422 in this embodiment drives the first stud 4121 to rotate in a first circumferential direction, such that the locking suture pressing block 4122 and the inner wall surface of the housing 411 press the first locking suture 310 and the second locking suture 320.

When it is necessary to cut the first locking suture 310 and the second locking suture 320, the first rotating shaft 422 rotates in a second circumferential direction opposite to the first circumferential direction. In this case, the first stud 4121 does not rotate in a pressed state, and the second stud 4131 rotates, such that the locking suture cutting block 4132 is located at a cutting position. Then the second rotating shaft 423 is driven to rotate by means of the second knob 425 in this embodiment, such that the second rotating shaft 423 drives the locking suture cutting block 4132 at the cutting position to rotate for cutting.

Figure 12:
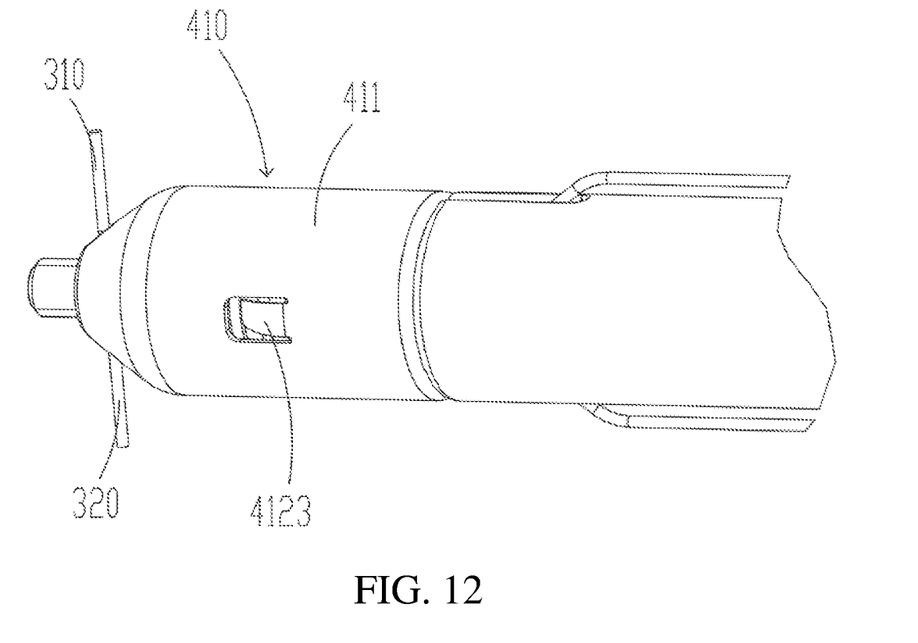
FIG. 12 is a schematic diagram of the external structure of a suture locking apparatus of a valve annulus contraction surgical system with an adjustable annulus contracting force at a single point according to an embodiment of the present application.

FIG. 12 is a schematic diagram of the external structure of a suture locking apparatus 410 of a valve annulus contraction surgical system with an adjustable annulus contracting force at a single point according to an embodiment of the present application. As shown in FIG. 12, generally speaking, after the first locking suture 310 and the second locking suture 320 are pressed by the locking suture pressing block 4122, a certain friction force exists, which, therefore, can restrict reversing of the first stud 4121 in the second circumferential direction, but the restricting effect is limited.

Therefore, the pressing assembly 412 in this embodiment further comprises a pressing anti-return elastic fastener 4123 mounted on the housing 411. By pressing this elastic fastener, the locking suture pressing block 4122 after suture locking can be locked, to prevent the locking suture pressing block from reversing with the first rotating shaft 422 in the second circumferential direction, and the second stud 4131 in this embodiment can thus be rotated out of the second threaded hole.

Figure 13:
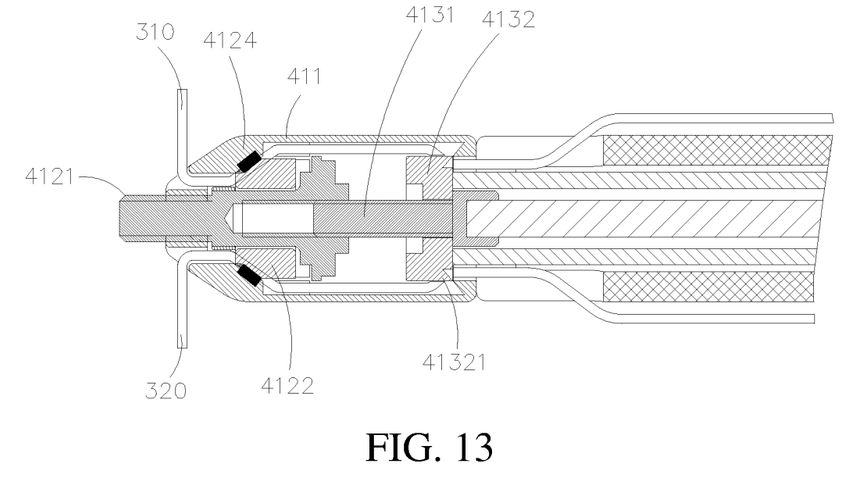
FIG. 13 is a schematic diagram of the internal structure of a suture locking apparatus of a valve annulus contraction surgical system with an adjustable annulus contracting force at a single point according to an embodiment of the present application.

FIG. 13 is a schematic diagram of the internal structure of a suture locking apparatus 410 of a valve annulus contraction surgical system with an adjustable annulus contracting force at a single point according to an embodiment of the present application. As shown in FIG. 13, the first locking suture 310 and the second locking suture 320 have been pressed by the locking suture pressing block 4122.

In order to increase locking forces on the first locking suture 310 and the second locking suture 320, the pressing assembly 412 in this embodiment further comprises a suture locking plate 4124 mounted to the inner wall surface of the housing 411 and opposite the locking suture pressing block 4122. When the first rotating shaft 422 of the suture locking operation handle 420 in this embodiment drives the first stud 4121 to rotate, the locking suture pressing block 4122 is driven to approach the suture locking plate 4124 to press the first locking suture 310 and the second locking suture 320.

Moreover, the locking suture pressing block 4122 and the suture locking plate 4124 may be provided with friction surfaces (not marked) having serrated cross-sections, so as to increase the friction force between the suture pressing assembly and the first locking suture 310 and the second locking suture 320 during locking and improve the suture locking stability.

In addition, in order to facilitate the cutting of the first locking suture 310 and the second locking suture 320, in this embodiment, a cross-sectional shape of a side of the locking suture cutting block 4132 that faces the third opening 4114 has a first annular tip 41321. Correspondingly, in this embodiment, a side wall of the housing 411 at the third opening 4114 is provided with a second annular tip 4115 facing the locking suture cutting block 4132; and the suture locking operation handle 420 is configured to drive the first annular tip 41321 to approach the second annular tip 4115 to a cutting position for performing rotary cutting.

Figure 14:
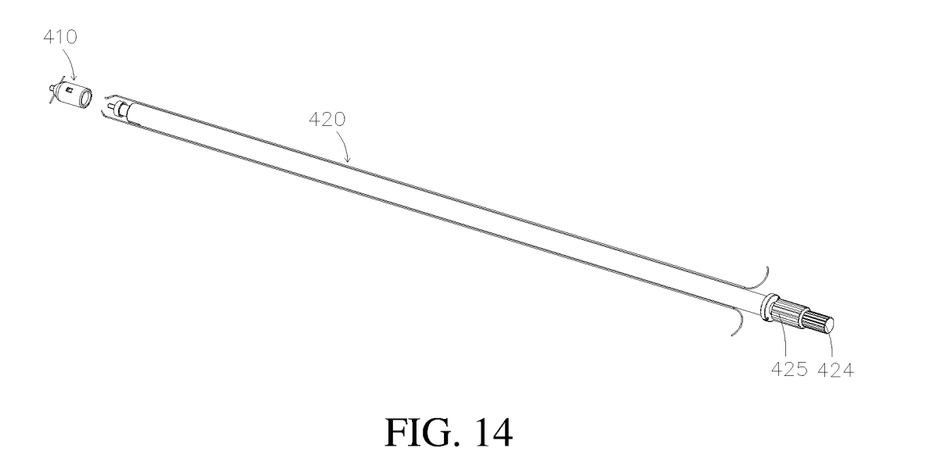
FIG. 14 is a schematic structural diagram of a suture locking device of a valve annulus contraction surgical system with an adjustable annulus contracting force at a single point according to an embodiment of the present application after a suture locking apparatus and a suture locking operation handle are separated.

FIG. 14 is a schematic structural diagram of a suture locking device 400 of a valve annulus contraction surgical system with an adjustable annulus contracting force at a single point according to an embodiment of the present application after a suture locking apparatus 410 and a suture locking operation handle 420 are separated. As shown in FIG. 14, when the second knob 425 drives the second stud 4131 to rotate in the second circumferential direction, the second stud 4131, the cutting assembly 413 and the suture locking operation handle 420 in this embodiment are disconnected from the first stud 4121 in the housing 411.

To sum up, the valve annulus contraction surgical system with an adjustable annulus contracting force at a single point according to the embodiments of the present application differs from an annulus contracting method using a traditional formed annulus in that the anchors 100 are implanted at several predetermined positions on the valve annulus, a locking suture is arranged on one side or either side of each of the anchors 100, the locking sutures are used to lock the anchors 100 in pairs, and since the level of locking of every two anchors 100 may be different, the level of locking of two anchors 100 may be arbitrarily adjusted according to the shape of the valve annulus in such a way that a valve orifice can be completely covered by a valve after the adjustment, thereby ensuring a therapeutic effect. Moreover, the structures of the implantation device 200 and the suture locking device 400 are optimized, to facilitate the implantation of the anchors 100 and the suture locking and cutting operations.

In the above description of the present application, it should be noted that "a plurality of" means two or more, unless otherwise specified. The orientation or position relationship indicated by the terms "upper", "lower", "left", "right", "inner", "outer", etc. is only for the convenience of describing the present application and simplifying the description, rather than indicating or implying that the device or element referred to must have a particular orientation or be constructed and operated in a particular orientation, and therefore should not be construed as a limitation on the present application. In addition, the terms such as "first", "second" and "third" are for descriptive purposes only and should not be construed as indicating or implying relative importance.

The orientation terms in the following description all indicate directions shown in the accompanying drawings, and do not limit the specific structure in the present application. In the description of the present application, it should also be noted that, the terms "mount", "connected", and "connect" should be interpreted in a broad sense unless explicitly defined and limited otherwise. For example, the terms may mean a fixed connection, a detachable connection or an integral connection; and may mean a direct connection, or an indirect connection by means of an intermediate medium. For those of ordinary skill in the art, the specific meanings of the terms mentioned above in the present application can be construed according to specific circumstances.

Although the present application has been described with reference to the preferred embodiments, various modifications can be made, and equivalents can be provided to substitute for the components therein without departing from the scope of the present application. In particular, the technical features mentioned in the embodiments can be combined in any manner, provided that there is no structural conflict. The present application is not limited to the specific embodiments disclosed herein but includes all the technical solutions that fall within the scope of the claims.

What is claimed is:

1. A valve annulus contraction surgical system with an adjustable annulus contracting force at a single point, comprising:

a plurality of anchors, wherein a suture locking tab is arranged on at least one of two sides of each of the anchors;

an implantation device configured to implant the anchors into a valve annulus;

a plurality of groups of locking sutures, wherein each group of locking sutures comprises a first locking suture and a second locking suture, one end of the first locking suture is connected to the suture locking tab of one of two adjacent anchors, and one end of the second locking suture is connected to the suture locking tab of the other of the two adjacent anchors; and a suture locking device configured to lock and fix the other end of the first locking suture and the other end of the second locking suture, wherein the suture locking device comprises a suture locking apparatus and a suture locking operation handle; the suture locking apparatus is configured to lock and cut off the first locking suture and the second locking suture of the group of locking sutures under the driving of the suture locking operation handle;

the suture locking apparatus comprises a housing, a pressing assembly, and a cutting assembly; the pressing assembly, the cutting assembly and the suture locking operation handle are connected to one another in sequence; the suture locking operation handle is configured to drive the pressing assembly to lock the first locking suture and the second locking suture, and drive the cutting assembly to cut the first locking suture and the second locking suture; the housing is provided at one end with a first threaded hole, a first opening for entry of the first locking suture, and a second opening for the second locking suture to pass through, and at the other end with a third opening for the first locking suture and the second locking suture to extend out; the pressing assembly comprises a first stud and a locking suture pressing block; the first stud is connected to the first threaded hole, and is provided with a second threaded hole; the locking suture pressing block is sleeved on the first stud; the first stud is driven by the suture locking operation handle to rotate, such that the locking suture pressing block and an inner wall surface of the housing lock the first locking suture and the second locking suture; the cutting assembly comprises a second stud and a locking suture cutting block; the locking suture cutting block is rotatably sleeved on the second stud, and the second stud is connected to the second threaded hole; the suture locking operation handle drives the locking suture cutting block to rotate to cut the first locking suture and the second locking suture, and the suture locking operation handle drives the second stud to rotate such that the second stud and the locking suture cutting block are separated from the housing; a cross-sectional shape of a side of the locking suture cutting block that faces the third opening has a first annular tip; a side wall of the housing at the third opening is provided with a second annular tip facing the locking suture cutting block; and the suture locking operation handle is configured to drive the first annular tip to approach the second annular tip to a cutting position for performing rotary cutting.

2. The valve annulus contraction surgical system with an adjustable annulus contracting force at a single point according to claim 1, characterized in that
each of the anchors comprises a mating portion and an implantable portion that are connected to each other, wherein the mating portion is configured to be connected to and mated with the implantation device, and the implantable portion is a spiral thread; and
the suture locking tab is provided with a plurality of first connecting holes for the spiral thread in a length direction of the suture locking tab, and is provided with a second connecting hole for the first locking suture or the second locking suture to pass through.

3. The valve annulus contraction surgical system with an adjustable annulus contracting force at a single point according to claim 1, characterized in that
the implantation device comprises an implantation tube, an implantation operation assembly, a delivery cable, a puncture needle, and a puncture operation assembly;
the delivery cable is partially located in the implantation tube, and is driven by the implantation operation assembly such that the anchor is moved to and released at an opening of the implantation tube;
the puncture needle penetrates the delivery cable, and has one end provided with a tip, and the other end connected to the puncture operation assembly; and
the puncture operation assembly is configured to drive the tip to extend out of the opening of the implantation tube.

4. The valve annulus contraction surgical system with an adjustable annulus contracting force at a single point according to claim 3, characterized in that
the puncture operation assembly comprises a puncture handle and a limiting mechanism;
the puncture handle is connected to an end of the puncture needle that faces away from the tip; and
the limiting mechanism is located between the implantation operation assembly and the puncture handle, and is connected to an end of the delivery cable that is located outside the implantation tube,
wherein the limiting mechanism is configured to limit a length of the puncture needle extending out of the opening of the implantation tube.

5. The valve annulus contraction surgical system with an adjustable annulus contracting force at a single point according to claim 1, characterized in that
the suture locking operation handle comprises an outer tube, a first rotating shaft, and a second rotating shaft;
the first rotating shaft is mounted in the outer tube, and has one end connected to the second stud;
the second rotating shaft is hollow, is sleeved on the first rotating shaft, and has one end connected to the locking suture cutting block,
wherein the first rotating shaft drives the first stud to rotate in a first circumferential direction, such that the locking suture pressing block and the inner wall surface of the housing press the first locking suture and the second locking suture; the first rotating shaft rotates in a second circumferential direction opposite to the first circumferential direction, such that the locking suture cutting block is located at a cutting position; and the second rotating shaft is configured to drive the locking suture cutting block at the cutting position to rotate for cutting.

6. The valve annulus contraction surgical system with an adjustable annulus contracting force at a single point according to claim 1, characterized in that
a suture locking plate opposite the locking suture pressing block is mounted at the inner wall surface of the housing; and
the suture locking operation handle is configured to drive the locking suture pressing block to approach the suture locking plate, so as to press the first locking suture and the second locking suture.

\* \* \* \* \*